United States Patent [19]
Edwards et al.

[11] Patent Number: 6,160,006
[45] Date of Patent: Dec. 12, 2000

[54] 6',7'-DIHYDROXYBERGAMOTTIN, A CYTOCHROME P450 INHIBITOR IN GRAPEFRUIT

[75] Inventors: David J. Edwards, LaSalle, Canada; Patrick M. Woster, Canton, Mich.

[73] Assignee: Wayne State University, Detroit, Mich.

[21] Appl. No.: 08/951,330

[22] Filed: Oct. 16, 1997

Related U.S. Application Data

[60] Provisional application No. 60/028,961, Oct. 18, 1996, and provisional application No. 60/054,332, Jun. 24, 1997.

[51] Int. Cl.[7] .................... A61K 31/352; C07D 493/06
[52] U.S. Cl. ........................................... 514/455; 549/282
[58] Field of Search ............................ 514/455; 549/282

[56] References Cited

PUBLICATIONS

Bailey, D.G. et al., "Grapefruit juice–felodipine interaction: Mechanism, predictability, and effect of naringin," *Clin. Pharmacol. Ther.* 53(6):637–642 (1993).

Bailey, D.G. et al. "Effect of grapefruit juice and naringin on nisoldipine pharmacokinetics," *Clin. Pharmacol. Ther.* 54(6):589–594 (1993).

(List continued on next page.)

*Primary Examiner*—Johann Richter
*Assistant Examiner*—Taofiq A. Solola
*Attorney, Agent, or Firm*—Lahive & Cockfield, LLP

[57] ABSTRACT

The present invention provides a composition and methods for inhibiting cytochrome P450 enzyme activity and in particular, inhibiting the activity of the cytochrome P450 3A sub-family of enzymes, specifically, CYP3A4. The present invention provides 6',7'-dihydroxybergamottin, a furanocoumarin, as the compound primarily responsible for the inhibitory effects of grapefruit juice on cytochrome P450 enzyme activity. The present invention also provides a novel synthesis scheme for 6',7'-dihydroxybergamottin.

25 Claims, 3 Drawing Sheets

OTHER PUBLICATIONS

Bailey, D.G. et al., "Interaction of citrus juices with felodipine and nifedipine," *Lancet* 337:268–269 (1991).

Benton, R. et al., "Grapefruit Juice Alters Terfenadine Pharmacokinetics Resulting In Prolongation Of QTc," *Clin. Pharmacol. Ther.* 55:146 (1994).

Block, G. et al., "Fruit, Vegetables, and Cancer Prevention: A Review of the Epidemiological Evidence," *Nutri. Cancer* 18:1–29 (1992).

Brian, W.R. et al., "Catalytic Activities of Human Liver Cytochrome P–450 IIIA4 Expressed in *Saccharomyces cerevisiae*," *Biochem.* 29:11280–11292 (1990).

Burke, M.D. et al., "Ethoxy–, Pentoxy– And Benzyloxyphenoxazones And Homologues: A Series Of Substrates To Distinguish Between Different Induced Cytochromes P450," *Biochem. Pharmacol.* 34:3337–3345 (1985).

Chadwick, R.W. et al., "Role Of The Gastrointestinal Mucosa And Microflora In The Bioactivation Of Dietary And Environmental Mutagens Or Carcinogens," *Drug Metab. Rev.* 24:425–492 (1992).

Chatterjee, A. et al., "The Synthesis Of Bergamottin," *J. Chem. Soc.* 428:2246–2247 (1961).

Corcoran, G.B. et al., "Effects of N–Acetylcysteine on the Disposition and Metabolism of Acetaminophen in Mice," *J. Pharmcol. Exp. Ther.* 232:857–863 (1985).

Cornish–Bowden, A., "A Simple Graphical Method for Determining the Inhibition Constants of Mixed, Uncompetitive and Non–Competitive Inhibitors," *Biochem. J.* 137:143–144 (1974).

Dixon, M., "The Determination of Enzyme Inhibitor Constants," *Biochem. J.* 55:170–171 (1953).

Dreyer, D.L. et al., "Coumarins Of *Citrus Macroptera*," *Phytochemistry* 12:3011–3013 (1973).

Ducharme, M.P. et al., "Trough concentrations of cyclosporine in blood following administration with grapefruit juice," *Br. J. Clin. Pharmacol.* 36:457–459 (1993).

Ducharme M.P. et al., "Disposition of intravenous and oral cyclosporine after administration with grapefruit juice," *Clin. Pharmacol. Ther.* 57:485–491 (1995).

Edwards, D.J. et al., "Identification Of 6',7'–Dihydroxybergamottin, A Cytochrome P450 Inhibitor, In Grapefruit Juice," *Drug Metab. Dispos.* 24:1287–1290 (1996).

Edwards, D.J. et al., "Naringin And Naringenin Are Not The Primary CYP3A Inhibitors In Grapefruit Juice," *Life Sciences* 59:1025–1030 (1996).

Ferguson, L.R., "Antimutagens as cancer chemopreventive agents in the diet," *Mutat. Res.* 307:395–410 (1994).

Fouin–Fortunet, H. et al., "Inactivation of Cytochrome P–450 by the Drug Methoxsalen," *J. Pharmacol. Exp. Ther.* 236:237–247 (1986).

Fuhr, U. et al., "Inhibitory effect of grapefruit juice and its bitter principal, naringenin, on CYP1A2 dependent metabolism of caffeine in man," *Br. J. Clin. Pharmacol.* 35:431–436 (1993).

Gonzalez, F.J. et al., "Role Of Human Cytochromes P450 In The Metabolic Activation Of Chemical Carcinogens And Toxins," *Drug Metab. Rev.* 26:165–183 (1994).

Greenlee, W.F. et al., "An Improved Assay Of 7–Ethoxycoumarin Odeethylase Activity: Induction Of Hepatic Enzyme Activity In C57BL/6J And DBA/2J Mice By Phenobarbital, –3–Methylcholanthrene And 2,3,7,8–Tetrachlorodibenzo–p–Dioxin," *J. Pharmacol. Exp. Ther.* 205:596–605 (1978).

Greenwald, P. et al., "New Directions In Dietary Studies In Cancer: The National Cancer Institute," *Adv. Exp. Med. Biol.* 369:229–239 (1995).

Guengerich, F.P. et al., "In vitro inhibition of dihydropyridine oxidation and aflatoxin $B_1$ activation in human liver microsomes by naringenin and other flavonoids," *Carcinogenesis* 11:2275–2279 (1990).

Guengerich, F.P., "Roles of Cytochrome P–450 Enzymes in Chemical Carcinogenesis and Cancer Chemotherapy," *Cancer Res.* 48:2946–2954 (1988).

Habig, W.H. et al., "Glutathione S–Transferases," *J. Biol. Chem.* 249:7130–7139 (1974).

Hebert, M.F. et al., "Bioavailability of cyclosporine with concomitant rifampin administration is markedly less than predicted by hepatic enzyme induction," *Clin. Pharmacol. Ther.* 52:453–457 (1992).

Hertog, M.G.L. et al., "Dietary antioxidant flavonoids and risk of coronary heart disease: the Zutphen Elderly Study," *Lancet* 342:1007–1011 (1993).

Hukkinen, S.K. et al., "Pharmacokinetics And Drug Disposition—Plasma concentrations of triazolam are increased by concomitant ingestion of grapefruit juice," *Clin. Pharmacol. Ther.* 58:127–131 (1995).

Keogh, A. et al., "Ketoconazole To Reduce The Need For Cyclosporine After Cardiac Transplantation," *N. Engl. J. Med.* 333:628–633 (1995).

Kimura, R.E. et al., "Portal Venous and Aortic Glucose and Lactate Changes in a Chronically Catheterized Rat," *Pediatr.Res.* 23:235–240 (1988).

Kronbach, T. et al., "Cyclosporine metabolism in human liver: Identification of a cytochrome P–450III gene family as the major cyclosporine–metabolizing enzyme explains interactions of cyclosporine with other drugs," *Clin. Pharmac. Ther.* 43:630–635 (1988).

Kupferschmidt, H.H.T. et al., "Interaction between grapefruit juice and midazolam in humans," *Clin. Pharmacol. Ther.* 58(1):20–28 (1995).

Lin, J.H., "Species Similarities And Differences In Pharmacokinetics," *Drug Metab. Dispos.* 23:1008–1021 (1995).

Lundahl, J. et al., "Relationship between time of intake of grapefruit juice and its effect on pharmacokinetics and pharmacodynamics of felodipine in healthy subjects," *Eur. J. Clin. Pharmacol.* 49:61–67 (1995).

Mays, D.C. et al., "Methoxsalen is a potent inhibitor of the metabolism of caffeine in humans," *Clin. Pharmacol. Ther.* 42(6):621–626 (1987).

Merkel, U. et al., "Grapefruit juice inhibits 7–hydroxylation of coumarin in healthy volunteers," *Eur. J. Clin. Pharmacol.* 46:175–177 (1994).

Miniscalco, A. et al., "Inhibition of Dihydropyridine Metabolism in Rat and Human Liver Microsomes by Flavonoids Found in Grapefruit Juice," *J. Pharmacol. Exp. Ther.* 261(3):1195–1199 (1992).

Olkkola, K.T. et al., "A potentially hazardous interaction between erythromycin and midazolam," *Clin. Pharmacol. Ther.* 53:298–305 (1993).

Peter, R. et al., "Hydroxylation of Chlorzoxazone as a Specific Probe for Human Liver Cytochrome P–450IIE1," *Chem. Res. Toxicol.* 3:566–573 (1990).

Raftogianis, R.B. et al., "Effect of Lipid–Free Total Parenteral Nutrition on Hepatic Drug Conjugation in Rats," *J. Pharmacol. Exp. Ther.* 276:602–608 (1996).

Rashid, J. et al., "Quercetin, an in vitro inhibitors of CYP3A, does not contribute to the interaction between nifedipine and grapefruit juice," *Br. J. Clin. Pharmacol.* 36:460–463 (1993).

Ritter, J.K. et al., "Induction And Inhibition Of Rat Hepatic Drug Metabolism By N–Substituted Imidazole Drugs," *Drug Metab. Dispos.* 15(3):335–343 (1987).

Schonberg, A. et al., "Furo–chromones and –Coumarins (X): On the Constitution of Prangenin," *J. Am. Chem. Soc.* 77:2563–2564 (1955).

Shimada T. et al., "Evidence for cytochrome P–450$_{NF}$, the nifedipine oxidase, being the principal enzyme involved in the bioactivation of aflatoxins in human liver," *Proc. Natl. Acad. Sci. USA* 86(1):462–465 (1989).

Shimada, T. et al., "Interindividual Variations in Human Liver Cytochrome P–450 Enzymes Involved in the Oxidation of Drugs, Carcinogens and Toxic Chemicals: Studies with Liver Microsomes of 30 Japanese and 30 Caucasians," *J. Pharmacol. Exp. Ther.* 270(1):414–423 (1994).

Siess, M.–H. et al., "Heterogenous Effects of Natural Flavonoids on Monooxygenase Activities in Human and Rat Liver Microsomes," *Toxicol. Appl. Pharmacol.* 130:73–78 (1995).

Sonderfan, A.J. et al., "Regulation of Testosterone Hydroxylation by Rat Liver Microsomal Cytochrome P–450," *Arch. Biochem. Biophys.* 255(1):27–41 (1987).

Soons, P.A. et al., "Grapefruit juice and cimetidine inhibit stereoselective metabolism of nitrendipine in humans," *Clin. Pharmacol. Ther.* 50(4):394–403 (1991).

Tatum, J.H. et al., "Coumarins And Psoralens In Grapefruit Peel Oil," *Phytochemistry* 18:500–502 (1979).

Wakabayashi, K. et al., "Food–derived Mutagens and Carcinogens," *Cancer Res.* 52:2092s–2098s (1992).

Watkins, P.B. et al., "Identification of Glucocorticoid–inducible Cytochromes P–450 in the Intestinal Mucosa of Rats and Man," *J. Clin. Invest.* 80:1029–1036 (1987).

Wattenberg, L.W., "Inhibition of Carcinogenesis by Minor Dietary Constituents," *Cancer Res.* 52:2085s–2091s (1992).

Yun, C–H. et al., "Non–specific inhibition of cytochrome P450 activies by chlorophyllin in human and rat liver microsomes," *Carcinogenesis* 16:1437–40 (1995).

6',7'-DIHYDROXYBERGAMOTTIN, A CYTOCHROME P450 INHIBITOR IN GRAPEFRUIT

RELATED APPLICATIONS

This application is a continuation of provisional application Ser. Nos. 60/028,961, filed Oct. 18, 1996 and 60/054,332, filed Jun. 24, 1997, herein expressly incorporated by reference.

SPONSORSHIP

Work on this invention was sponsored in part by National Institute of Environmental Health Sciences EHS Center Grant 1 P30-ES06639. The Government has certain rights in the invention.

FIELD OF THE INVENTION

The present invention relates generally to a cytochrome P450 inhibitor found in grapefruit juice and, in particular, 6',7'-dihydroxybergamottin and methods of making and using same.

BACKGROUND OF THE INVENTION

Humans are continuously exposed to potential carcinogens in the diet. Such compounds may be natural constituents of food (plant alkaloids), contaminants (mycotoxins, pesticides) or formed through food preparation (heterocyclic amines). Chadwick, R. W. et al., *Drug Metab. Rev.* 24:425–492 (1992) and Wakabayashi, K. et al., *Cancer Res.* 52:2092s–2098s (1992). Over 90% of carcinogenic substances, however, are not genotoxic in their native form but require activation to the ultimate carcinogen. Enzymes of the cytochrome P450 family are highly concentrated in the gut wall (in particular the CYP3A sub-family of enzymes) and liver and play a significant role in this process. Chadwick, R. W. et al., *Drug Metab. Rev.* 24:425–492 (1992); Guengerich, F. P., *Cancer Res.* 48:2946–2954 (1988) and Gonzalez, F. J. et al., *Drug Metab. Rev.* 26:165–183 (1994). Activation of numerous procarcinogens including aflatoxin $B_1$, 2-aminofluorene and 3-methylcholanthrene by cytochrome P450 enzymes has been demonstrated using the Salmonella mutagenicity assay, cell transformation in culture and alterations in DNA. Inducers of cytochrome P450 activity enhance formation of genotoxic metabolites and increase the rate of tumor formation in animal models. Furthermore, variation in cytochrome P450 activity due to either genetic or environmental reasons has been found to correlate with genotoxin formation. Chadwick, R. W. et al., *Drug Metab. Rev.* 24:425–492 (1992).

Epidemiologic studies have consistently demonstrated that diet has a significant influence on the risk of developing cancer. Greenwald, P. et al., *Adv. Exp. Med. Biol.* 369:229–239 (1995). Most striking is the observation that diets high in vegetables and fruits appear to lower cancer risk. Block, G. et al., *Nutr. Cancer* 18:1 (1992). The mechanism by which foods such as citrus fruits serve as chemopreventive agents is not precisely known. Such fruits contain numerous minor dietary components including flavonoids, carotenoids and coumarins which when fed in purified form to experimental animals appear to reduce the carcinogenic response. Wattenberg, L. W., *Cancer Res.* 52:2085s–2091s (1992). These compounds may act as antioxidants, alter the ability to repair damaged DNA, block mutagens from reaching target tissues or affect the formation of the activated mutagen by enzymes such as cytochrome P450. Ferguson, L. R., *Mutat. Res.* 307:395–410 (1994). It has recently been found that chlorophyllin, a potent antimutagen present in many fruits and vegetables, acts primarily through non-specific inhibition of cytochrome P450 activity. Yun, C-H. et al., *Carcinogenesis* 16:143–740 (1995). It is this mechanism which is of particular interest in examining the role of naturally-occurring compounds from citrus fruit in cancer prevention since research over the past five years has demonstrated that grapefruit juice is a powerful inhibitor of cytochrome P450.

It has also been recently found that grapefruit juice increases bioavailability of drugs. Bailey and co-workers were the first to report that oral administration of the calcium channel antagonists nifedipine and felodipine with grapefruit juice resulted in several-fold increases in bioavailability and blood concentrations. Bailey, D. G. et al., *Lancet* 337:268–269 (1991). Since these drugs are highly metabolized on first-pass through the gut wall or liver, the increased bioavailability was attributed to impaired cytochrome P450 activity. Subsequent studies have demonstrated impaired metabolism of triazolam, midazolam, terfenadine and cyclosporine in the presence of grapefruit juice. Hukkinen, S. K. et al., *Clin. Pharmacol. Ther.* 58:127–131 (1995); Kupferschmidt, H. H. T. et al., *Clin. Pharmacol. Ther.* 58:20–28 (1995); Benton, R., et al., *Clin. Pharmacol. Ther.* 55:146 (1994); Ducharme, M. P. et al., *Br. J. Clin. Pharmacol.* 36:457–459 (1993) and Ducharme M. P. et al., *Clin. Pharmacol. Ther.* 57:485–491 (1995). All of these drugs are metabolized by CYP3A4, the most abundant of the cytochrome P450 enzymes accounting for approximately 30% of the P450 content of the liver and 70% in the gut wall. Shimada, T. et al., *J. Pharmacol. Exp. Ther.* 270:414–423 (1994) and Watkins, P. B. et al., *J. Clin. Invest.* 80:1029 (1987). This enzyme is involved in the activation of a number of carcinogens including aflatoxin $B_1$. Guengerich, F. P., *Cancer Res.* 48:2946–2954 (1988) and Gonzalez, F. J. et al., *Drug Metab. Rev.* 26:165–183 (1994). Grapefruit juice has also been reported to inhibit the metabolism of caffeine and coumarin, substrates for the CYP1A2 and CYP2A6 enzymes respectively, suggesting that inhibition is not limited to a single cytochrome P450 enzyme. Fuhr, U. et al., *Br. J. Clin. Pharmacol.* 35:431–436 (1993) and Merkel, U. et al., *Eur. J. Clin. Pharmacol.* 46:175–177 (1994). Both of these enzymes are also known to participate in the formation of mutagenic metabolites. Gonzalez, F. J. et al., *Drug Metab. Rev.* 26:165–183 (1994).

Grapefruit juice was found to have a much more pronounced effect on the bioavailability of oral cyclosporine compared to intravenous (IV) cyclosporine. Since cyclosporine is highly extracted by the gut wall and poorly extracted by the liver (Hebert, M. F. et al., *Clin. Pharmacol. Ther.* 52:453–457 (1992)), this suggests that grapefruit juice predominantly inhibits gut wall cyclosporine metabolism. Ducharme M. P. et al., *Clin. Pharmacol. Ther.* 57:485–491 (1995). The hypothesis that the inhibitor in grapefruit juice is primarily active in the gut is supported by studies with midazolam. Grapefruit juice had no effect on the systemic clearance of intravenous midazolam but increased oral bioavailability by 50%. Kupferschmidt, H. H. T. et al., *Clin. Pharmacol. Ther.* 58:20–28 (1995). In contrast, oral administration of erythromycin impaired the metabolism of midazolam after both oral and IV administration. Olkkola, K. T. et al., *Clin. Pharmacol. Ther.* 53:298–305 (1993). Orally administered erythromycin is systemically available and inhibits liver P450 activity. The fact that erythromycin inhibits IV midazolam while grapefruit juice does not suggests that the inhibitor in grapefruit juice is either not absorbed into the systemic circulation in significant enough quantities to affect liver P450 activity or that its effects on P450 are too short-lived to affect hepatic clearance. A transient or short-lived effect of grapefruit juice seems unlikely given the findings of Lundahl, J. et al., *Eur. J. Clin. Pharmacol.* 49:61 (1995), who reported impaired first-pass metabolism of oral felodipine when grapefruit juice was ingested up to 24 hours before administration of the drug. The most plausible explanation for the lack of effect of grapefruit juice on IV administered substrates with a prolonged effect on oral compounds is that the inhibitor is either not bioavailable, is absorbed slowly from the gut or binds to gut P450 in such a way as to inhibit metabolism for many hours. Inhibition of gut wall cytochrome P450 may be a more effective chemoprotective mechanism than inhibition of hepatic enzymes since many orally ingested procarcinogens will have been activated to their mutagenic form prior to reaching the liver.

A number of published reports have attempted to identify the active P450 enzyme inhibitor in grapefruit juice, a difficult task given that grapefruit forms one of the most complete metabolic grids in a single plant tissue, with dozens of polyphenolic compounds presenting different chemical classes. Most have focused on the flavonoids since several of these compounds are known inhibitors of cytochrome P450 and grapefruit juice contains high concentrations of flavonoids such as naringin (concentrations up to 500 mg/L) and quercetin. However, naringin is a weak inhibitor of oxidative metabolism in vitro (Miniscalco, A. et al., *J. Pharmacol. Exp. Ther.* 261:1195–1199 (1992) and Guengerich, F. P. et al., *Carcinogenesis* 11:2275–2279 (1990)) and the administration of naringin in aqueous solution or capsule form to human subjects did not significantly affect the disposition of substrates for CYP3A4. Bailey, D. G. et al., *Clin. Pharmacol. Ther.* 53:637–442 (1993) and Bailey, D. G. et al., *Clin. Pharmacol. Ther.* 54:589–594 (1993). A dose of quercetin far in excess of the typical amount contained in grapefruit juice also had no effect on cytochrome P450 activity. Rashid, J. et al., *Br. J. Clin. Pharmacol.* 36:46–463 (1993). A number of in vitro experiments confirm that while grapefruit juice exhibits potent inhibition of CYP3A, naringin and its aglycone naringenin do not significantly contribute to this effect. Edwards, D. J. et al. *Life Sciences* 59:1025–1030 (1996).

In summary, inhibition of cytochrome P450 enzyme activity and in particular, inhibition of the activity of the CYP3A sub-family of enzymes, is clearly of therapeutic importance. The co-administration of cyclosporine with a CYP3A enzyme inhibitor such as ketoconazole increases bioavailability and allows for the use of much lower oral doses of this expensive medication. Keogh, A. et al. *N. Engl. J. Med.* 333:628–633 (1995). In addition, as outlined above, these enzymes play a role in the activation of procarcinogens to their genotoxic form (Shimada T. et al., *Proc. Natl. Acad. Sci. USA* 86:462–465 (1989)), suggesting that a cytochrome P450 enzyme inhibitor ingested chronically could be useful in the prevention of cancer. It would thus be desirable to provide the compound in grapefruit juice responsible for inhibition of cytochrome P450 enzyme activity.

SUMMARY OF THE INVENTION

The present invention provides a composition and methods for inhibiting cytochrome P450 enzyme activity and in particular, inhibiting the activity of the CYP3A sub-family of enzymes, specifically, CYP3A4. The present invention provides 6',7'-dihydroxybergamottin, a furanocoumarin, as the compound primarily responsible for the inhibitory effects of grapefruit juice on cytochrome P450 activity. The composition of the present invention thus comprises 6',7'-dihydroxybergamottin preferably in an oral unit dosage form.

The present invention further provides methods of using 6',7'-dihydroxybergamottin generally comprising the treatment of a patient (in need of such treatment) with a therapeutically-effective amount of 6',7'-dihydroxybergamottin. The methods preferably include administration of 6',7'-dihydroxybergamottin in a pharmaceutically-acceptable vehicle via modes known to those skilled in the art, e.g. oral, intravenous, etc. The methods of the present invention may also include administration of 6',7'-dihydroxybergamottin in combination with at least one drug that is metabolized by cytochrome P450 enzymes, to increase the bioavailability of the drug(s). The present invention further includes methods of making 6',7'-dihydroxybergamottin.

Additional objects, advantages, and features of the present invention will become apparent from the following description, taken in conjunction with the accompanying drawings and claims.

BRIEF DESCRIPTION OF THE DRAWINGS

The various advantages of the present invention will become apparent to one skilled in the art by reading the following specification and subjoined claims and by referencing the following drawings in which:

DETAILED DESCRIPTION OF THE PREFERRED EMBODIMENTS

The present invention relates to a composition and methods for inhibiting cytochrome P450 enzyme activity and in particular, inhibiting CYP3A enzyme activity. The composition, 6',7'-dihydroxybergamottin, is a potent inhibitor of CYP3A activity and is primarily responsible for the effects of grapefruit juice on decreasing cytochrome P450 activity in humans. In accordance with the present invention, a therapeutically-effective amount of 6',7'-dihydroxybergamottin is formulated and administered to a patient to inhibit cytochrome P450 enzyme activity. The methods may also be used in combination with administration of any active agent, e.g. a drug such as cyclosporine, that is metabolized by cytochrome P450 enzymes, in particular CYP3A enzymes, to increase the bioavailability of the active agent. The methods of the present invention may also be used to reduce the activation of procarcinogens by inhibiting cytochrome P450 enzyme activity. The methods of the present invention thus find use in any patient (human or other mammal) wherein the inhibition of cytochrome P450 enzyme activity is desirable.

It should be appreciated that while this invention preferably contemplates oral administration of the composition of the present invention, nothing herein should be construed to limit the mode of delivery. Both oral and systemic routes of delivery may be appropriate, particularly in combination-therapy regimes, i.e. administration of 6',7'-dihydroxybergamottin in combination with an additional active agent. Further, it should also be appreciated that 6',7'-dihydroxybergamottin and any additional active agent need not be administered in the same manner, i.e., one may be administered orally while another may be administered systemically. It therefore follows that while the compositions selected for the methods of the present invention are preferably administered concomitantly, the administration need not be co-instantaneously. It is preferred that they be administered such that their therapeutic effects are synchronized or overlap. Based upon ease of treatment, however, in a highly preferred embodiment, the selected compositions are administered separately, in individual unit dosage form, including tablet and capsule.

It will be appreciated that the composition of the present invention may also be employed in a pharmaceutically-acceptable form such as an ester, salt, or as a prodrug. In addition, it will be appreciated that homologues and analogues of 6',7'-dihydroxybergamottin which also decrease cytochrome P450 enzyme activity, are further contemplated by the present invention. The synthesis schemes for 6',7'-dihydroxybergamottin provided herein may be readily adapted by those skilled in the art for the production of homologues and analogues of 6',7'-dihydroxybergamottin.

In practicing the methods of the present invention, the amount of 6',7'-dihydroxybergamottin to be administered (as well as any other active agents in the treatment regime) will vary with the patient being treated and will be monitored on a patient-by-patient basis by the physician or other healthcare provider. Generally, a therapeutically-effective amount of the compound of the present invention will be applied for a therapeutically-effective duration. By "therapeutically-effective amount" and "therapeutically-effective duration" is preferably meant an amount or duration effective to achieve a selected desired result in accordance with the present invention without undue adverse physiological effects or side effects; the desired result generally being a clinically observable increase in the bioavailability of certain active agents, i.e., drug(s), and/or the inhibition of cytochrome P450 activity.

It should be appreciated that duration of treatment according to the methods of the present invention will vary with many factors and will primarily depend upon the specific condition of the patient and the specific combination of agents employed. It should also be appreciated that treatment agents, dosage and duration will be interdependent and can be varied together in order to achieve an optimal clinical response. In addition, dosage and duration will also depend on the specific combination of agents employed.

The agents utilized in the compositions and methods of the present invention can be administered in accordance with the present invention in any pharmaceutically-acceptable carrier, preferably one which is both non-toxic and suitable for oral delivery. The compounds may be formulated for administration by procedures well-established in the pharmaceutical arts.

As set forth herein, 6',7'-dihydroxybergamottin is a potent CYP3A enzyme inhibitor in vitro with a concentration of about 1 to 2 $\mu$M being required to reduce CYP3A activity by about 50%, using enzyme expressed from transfected human CYP3A4 cDNA. Concentrations of 6',7'-dihydroxybergamottin in naturally occurring grapefruit juice are in the range of about 20 to 60 $\mu$M (10–30 mg/L). In unit dosage form, about 5 to about 20 mg of 6',7'-dihydroxybergamottin is preferred and about 10 mg 6',7'-dihydroxybergamottin is most preferred.

For example, a pharmaceutical preparation in unit dosage form adapted for administration to promote bioavailability of a drug of interest may be prepared comprising, per unit dosage, an effective non-toxic amount of 6',7'-dihydroxybergamottin within the range of from about 5 to about 20 mg. A pharmaceutical preparation may also be adapted to include both a therapeutically-effective amount of 6',7'-dihydroxybergamottin in addition to a therapeutically-effective amount of a drug of interest. As used herein, "drug of interest" or "active agent" is meant to include any drug metabolized by cytochrome P450 enzyme, and in particular, the P450 3A family of enzymes, preferably CYP3A4, wherein increased bioavailability of the drug is desirable. Such drugs include, but are not limited to, felodipine, triazolam, midazolam, terfenadine, cyclosporine, quinidine, nifedipine, ethinylestradiol, lovastatin, retinoic acid, steroids, taxol and verapamil.

Such unit dosage preparations may be adapted for oral administration as a tablet, capsule, liquid, powder, bolus or the like. They may likewise be prepared in unit dosage form in an ingestible or injectable form. Art-disclosed formulation ingredients such as tableting agents, colorants, flavorants, anti-oxidants, emollients, surface-active agents, encapsulation agents, and the like may also be employed.

The Specific Examples below further describe the compositions and methods of the present invention. These examples are for illustrative purposes only and are not intended in any way to limit the scope of the invention. Specific Example 1 describes the isolation, synthesis and activity of 6',7'-dihydroxybergamottin. Specific Example 2 describes an additional, and more efficient, synthesis scheme for 6',7'-dihydroxybergamottin. Specific Example 3 shows the inhibitory effect of 6',7'-dihydroxybergamottin on cytochrome P450 CYP3A4. Specific Example 4 describes the quantification of 6',7'-dihydroxybergamottin in naturally occurring juice, in vivo absorption and disposition of 6',7'-dihydroxybergamottin, and the effect of 6',7'-dihydroxybergamottin on enzyme activity. Specific Example 5 describes pharmaceutical methods of use of 6',7'-dihydroxybergamottin.

SPECIFIC EXAMPLE 1

Methods

Chemicals. Bergamottin was obtained from Indofine Chemical Company, Inc. (Somerville, N.J.). Testosterone, 6$\beta$-hydroxytestosterone and 11$\beta$-hydroxytestosterone were purchased from Steraloids Inc. (Wilton, N.H.). Ketoconazole was obtained from Janssen Pharmaceutica (Belgium). All other chemicals were supplied by Sigma Chemical Co. (St. Louis, Mo.).

Isolation of 6',7'-dihydroxybergamottin by TLC. Grapefruit juice prepared from frozen concentrate (Old South™, Lykes Pasco, Dade City, Fla.) was extracted into methylene chloride. Following evaporation of the organic phase, the residue was dissolved in a small volume of methylene chloride, applied to TLC plates (Silica Gel, 250 $\mu$M, Sigma Chemical Co.) and eluted with hexane:acetone (6:4). The $R_f$ for 6',7'-dihydroxybergamottin was 0.35 under these conditions. The compound of interest was isolated from the plates and re-chromatographed using a methylene chloride:acetone (3:2) solvent system ($R_f$=0.6). After extraction from the silica gel with ethyl acetate, 6',7'-dihydroxybergamottin was crystallized from a hexane:ethyl acetate mixture. Approximately 5 mg of 6',7'-dihydroxybergamottin was obtained from each liter of juice.

Synthesis of 6',7'-dihydroxybergamottin. 6',7'-dihydroxybergamottin was synthesized according to procedures described by Dreyer and Huey. Dreyer, D. L. et al., *Citrus Macroptera. Phytochem.* 12:3011–3013 (1973). The yield of 6',7'-dihydroxybergamottin from bergamottin was 16%.

Measurement of CYP3A Activity. CYP3A activity was assessed by measuring the formation rate of 6β-hydroxytestosterone from testosterone in dexamethasone-induced liver microsomes from male Sprague-Dawley rats (Human Biologics Inc., Phoenix, Az.) using incubation conditions identical to those described previously. Edwards, D. J. et al., *Life Sci.* 59:1025–1030 (1996). Liver microsomes from rats were studied since they have been reported to exhibit comparable inhibition to human liver microsomes in studies with other naturally occurring inhibitors such as the flavonoids. Siess, M.-H. et al., *Toxicol. Appl. Pharmacol.* 130:73–78 (1995). In addition, 6β-hydroxytestosterone formation was also measured in human lymphoblast microsomes containing CYP3A4 expressed from transfected human CYP3A4 cDNA (Gentest Corporation, Woburn, Mass.). 6β-hydroxytestosterone formation was linear with respect to incubation time, microsomal protein and substrate concentration over the incubation period.

HPLC Procedures and instrumentation. HPLC was used to quantitate 6β-hydroxytestosterone concentrations in metabolic experiments (Brian, W. R. et al., *Biochem.* 29:11280–11292 (1990)) and to measure the concentration of 6',7'-dihydroxybergamottin in grapefruit juice and orange juice. The internal standard (11β-hydroxytestosterone) was added to 0.5 ml of the incubation mixture (to measure 6β-hydroxytestosterone) or 0.3 ml of citrus juice (to measure 6',7'-dihydroxybergamottin). Methylene chloride (4 ml) was added and samples were vortex mixed for 2 minutes. After centrifugation, the organic phase was evaporated, the residue re-constituted in 200 μl of mobile phase (55% methanol in water) and injected (100 μl) onto the column (Partisil 5 ODS-3 25 cm $C_{18}$ column, Whatman Inc., Clifton, N.J.). A mobile phase flow rate of 1.2 ml/minute was used with detection of analytes at 254 nm (Waters 490E multiwavelength UV detector, Waters Corp., Milford, Mass.). Retention times for 6β-hydroxytestosterone, 11β-hydroxytestosterone, 6',7'-dihydroxybergamottin and testosterone were typically 7, 10, 16 and 20 minutes respectively. Standard curves for 6β-hydroxytestosterone were linear over the range of 2.5 to 20 μM. The coefficient of variation of the assay at a concentration of 10 μM was 6.5%. 6',7'-dihydroxybergamottin was measured over the range of 5 to 80 μM in juice.

Metabolic Experiments. Grapefruit juice (1 ml) was extracted into methylene chloride and, following evaporation of the organic phase, the residue was reconstituted in mobile phase and chromatographed by HPLC. Fractions of the HPLC eluent were collected at 3–4 minute intervals following injection, evaporated and the effect of the residue on 6β-hydroxytestosterone formation examined. The concentration of 6',7'-dihydroxybergamottin required to reduce the formation of 6β-hydroxytestosterone by 50% ($IC_{50}$) was measured by adding synthetic 6',7'-dihydroxybergamottin to the incubation mixture in concentrations ranging from 10 to 100 μM. For comparison, the $IC_{50}$ was also determined for ketoconazole and cimetidine. To evaluate the contribution of 6',7'-dihydroxybergamottin to the inhibition produced by grapefruit juice, the compound was added to orange juice at a concentration of 30 μM (similar to the concentration measured in grapefruit juice). After adjustment to pH 7.4 using sodium hydroxide, the juice was added to the incubation mixture and its effects on CYP3A activity compared to grapefruit juice, grapefruit juice extracted with methylene chloride to remove 6',7'-dihydroxybergamottin, orange juice and orange juice spiked with naringin. Edwards, D. J. et al., *Life Sci.* 59:1025–1030 (1996). The effect of these solutions on 6β-hydroxytestosterone formation was compared using analysis of variance (SYSTAT for Windows™, Version 5.0) with the Tukey test for post-hoc analysis ($p<0.05$ for significance).

Results

Figure 1A:
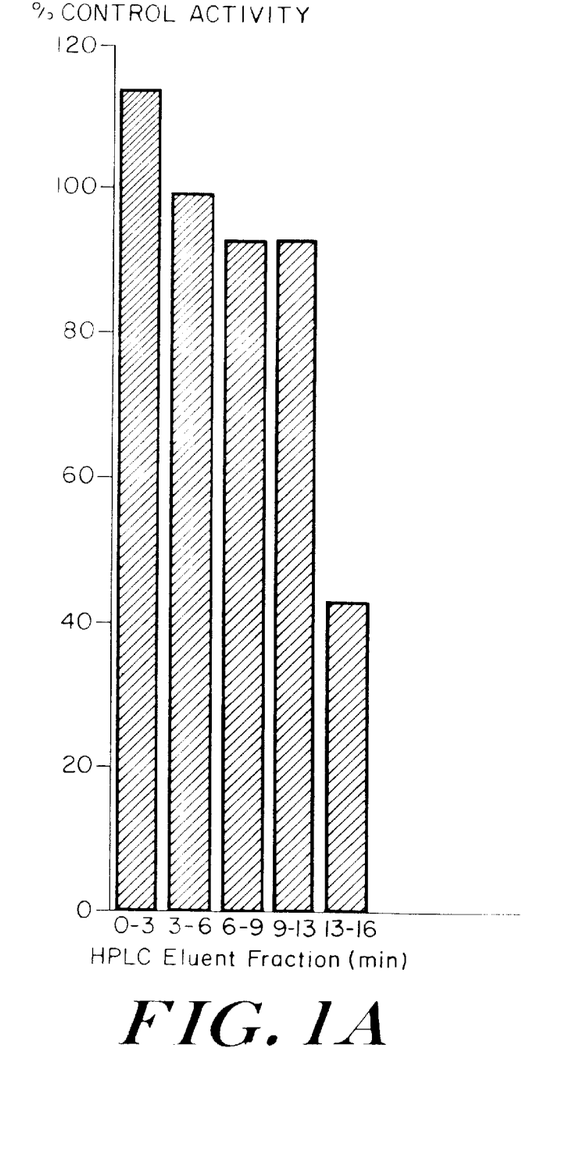
FIG. 1A is a bar graph showing CYP3A activity of microsomes incubated with fractions of HPLC eluent collected after injecting a methylene chloride extract of grapefruit juice.
Figure 1B:
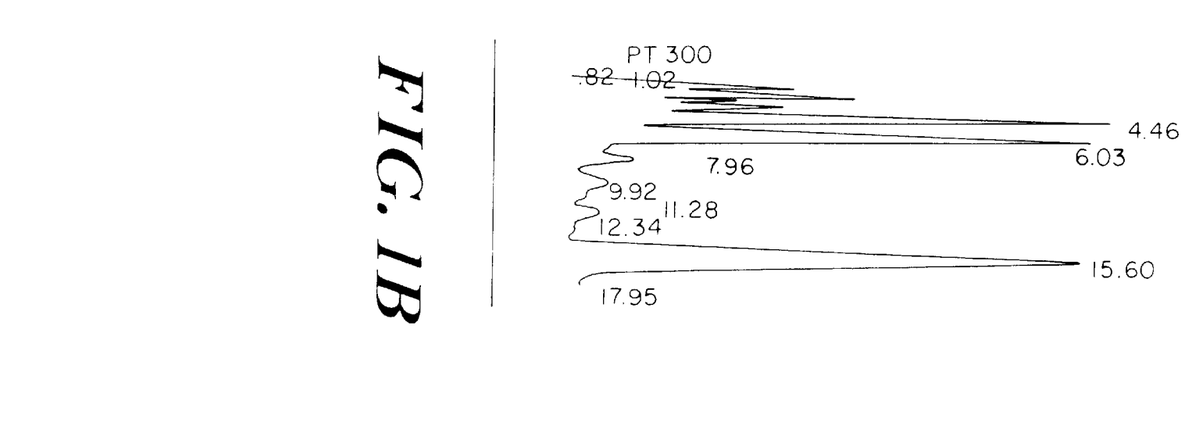
FIG. 1B is an HPLC chromatogram of a methylene chloride extract of grapefruit juice.
Figures 2A, 2B:
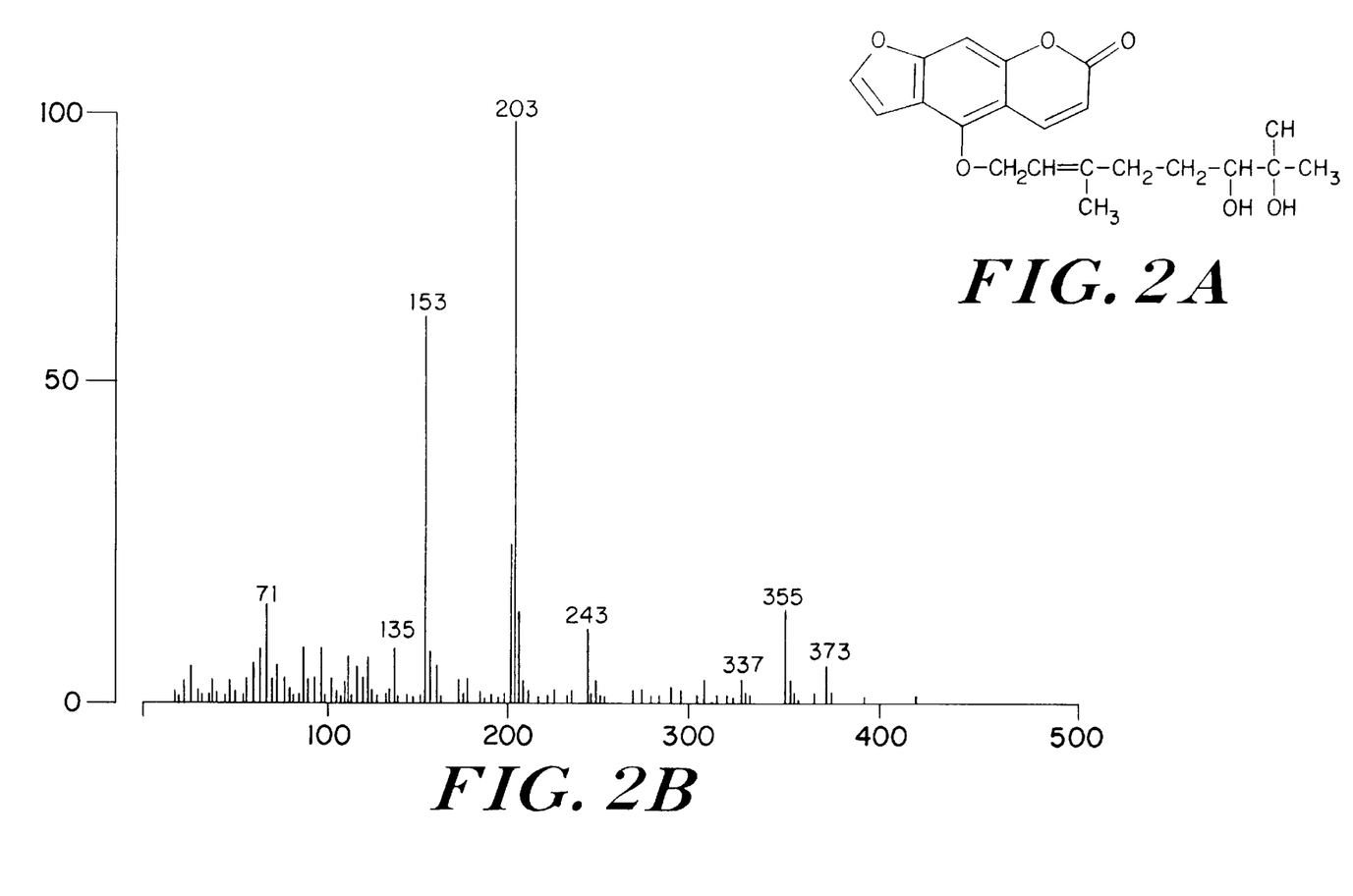
FIG. 2A is the chemical structure of 6',7'-dihydroxybergamottin.
FIG. 2B is the chemical-ionization mass spectrum of 6',7'-dihydroxybergamottin (MW 372, $C_{21}H_{24}O_6$)

Extraction of grapefruit juice into methylene chloride resulted in a chromatogram with a number of peaks following injection into the HPLC (FIG. 1B). However, only the eluent fraction containing the peak at 15.6 minutes was capable of inhibiting 6β-hydroxytestosterone formation (FIG. 1A). TLC was used to isolate the compound producing this peak. A carbon NMR spectrum suggested that the compound contained 21 carbon atoms. A proton NMR spectrum (General Electric GE300 NMR spectrometer) in deuterated chloroform matched that reported by Tatum and Berry (Tatum, J. H. et al., *Phytochemistry* 18:500–502 (1979)) for 6',7'-dihydroxybergamottin ($C_{21}H_{24}O_6$, MW 372), a furanocoumarin (psoralen) isolated from grapefruit peel oil (FIG. 2B). Dreyer and Huey (Dreyer, D. L. et al., *Citrus Macroptera. Phytochem.* 12:3011–3013 (1973)) had previously identified the same compound in *Citrus macroptera*, a fruit native to the south Pacific islands. 6',7'-dihydroxybergamottin had not been previously identified in grapefruit juice. Authentic 6',7'-dihydroxybergamottin was synthesized and found to be identical to the compound isolated from grapefruit juice by comparing the proton NMR spectrum, HPLC retention time, EI-MS and CI-MS data. The CI/MS indicated a parent (M+H) ion at m/z 373 with other prominent ions at m/z 355, m/z 203 and m/z 153 (FIG. 2B). The spectrum is dominated by the fragment (M+H) ion at 203 which represents 5-hydroxypsoralen (bergaptol). The peak at m/z 355 is due to the loss of water from the side chain of 6',7'-dihydroxybergamottin with the large fragment ion at m/z 153 being associated with the remainder of the geranyloxy side chain.

The concentration of 6',7'-dihydroxybergamottin required to inhibit 6β-hydroxytestosterone formation by 50% was found to be 25 μM in rat liver microsomes. The $IC_{50}$ was 1.8 μM for ketoconazole and more than 100 μM for cimetidine. 6',7'-dihydroxybergamottin was less potent than ketoconazole but was considerably more active than cimetidine. 6',7'-dihydroxybergamottin was much more potent in inhibiting the human CYP3A4 enzyme with an $IC_{50}$ of 1–2 μM.

Concentrations of 6',7'-dihydroxybergamottin in re-constituted frozen concentrated grapefruit juice (regular strength) were measured by HPLC and found to average 30 μM (12 mg/L). Orange juice (freshly squeezed from Navel oranges) contained no measurable 6',7'-dihydroxybergamottin. The formation of 6β-hydroxytestosterone in the presence of grapefruit juice and orange juice treated in order to vary the native concentration of 6',7'-dihydroxybergamottin is listed in Table 1. Orange juice was a much weaker inhibitor of CYP3A activity than grapefruit juice (p<0.05). There was no significant difference between the degree of inhibition produced by grapefruit juice and that produced by orange juice spiked with either synthetic 6',7'-dihydroxybergamottin or material extracted from grapefruit juice. Extraction with methylene chloride removed essentially all 6',7'-dihydroxybergamottin from grapefruit juice and reduced inhibitory activity to values comparable to control.

TABLE 1

Effect of Grapefruit Juice, Orange Juice and Orange Juice Spiked with 6',7'-dihydroxybergamottin or Naringin on 6β-hydroxytestosterone Formation in Rat Liver Microsomes

| Solution Tested (n = 5) | % of Control Activity (Mean ± SD) |
|---|---|
| Grapefruit Juice with 6',7'-dihydroxybergamottin 30 μM | 28.6 ± 1.7 |
| Orange Juice spiked with synthetic 6',7'-dihydroxybergamottin 30 μM | 31.6 ± 0.8 |
| Orange Juice spiked with extracted 6',7'-dihydroxybergamottin 30 μM | 34.7 ± 1.1 |
| Orange Juice spiked with naringin 450 mg/L | 60.4 ± 2.0* |
| Orange Juice | 62.2 ± 3.3* |
| Grapefruit Juice following organic extraction with methylene chloride | 82.9 ± 1.9* |

*Significantly different from grapefruit juice or orange juice containing 6',7'-dihydroxybergamottin

SPECIFIC EXAMPLE 2

Synthesis of 6',7'-dihydroxybergamottin

Figure 3:
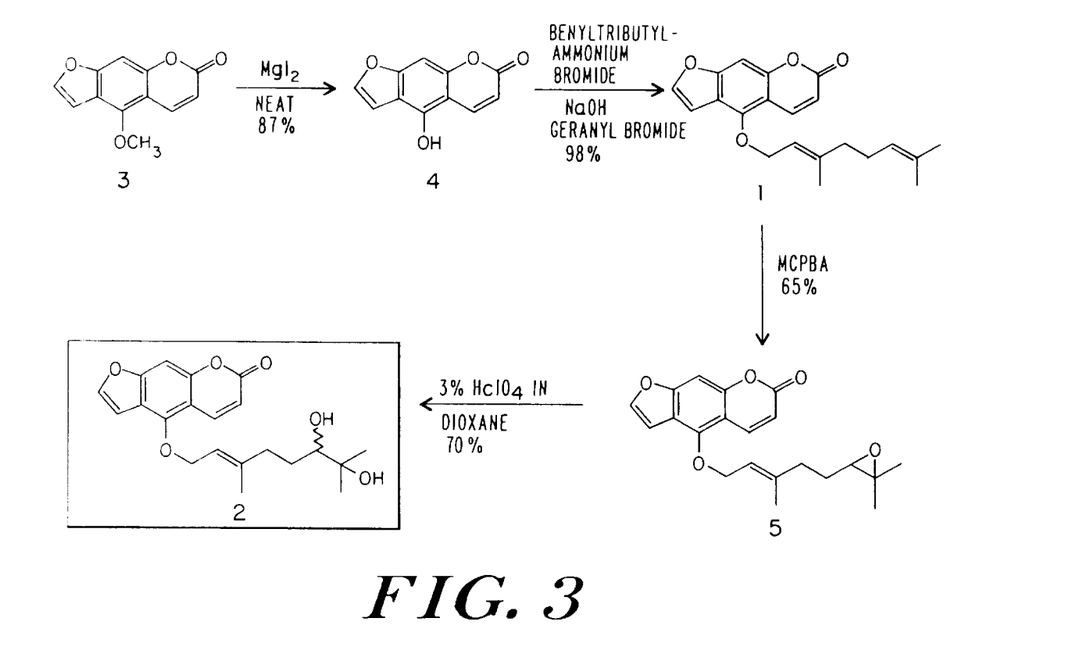
FIG. 3 is a an outline of a synthesis route for 6',7'-dihydroxybergamottin.

An efficient synthesis of 6',7'-dihydroxybergamottin is provided and outlined in FIG. 3. The commercially available furanocoumarin bergapten (indicated as compound 3 in FIG. 3) was demethylated using a previously published procedure (Miniscalco, A. et al., J. Pharmac Exp. Ther. 261:1195–1199 (1992)), producing the corresponding phenolic derivative bergaptol (indicated as compound 4 in FIG. 3). Geranylation of bergaptol (4) under phase transfer conditions (geranyl bromide, benzyl tributylammonium bromide, NaOH) then afforded bergamottin (indicated as compound 1 in FIG. 3) in 98% yield. Subsequent treatment of bergamottin (1) with m-chloroperbenzoic acid then resulted in selective epoxidation of the terminal double bond of the geranyl sidechain, affording bergamottin-6,7-epoxide 5 in 65% yield. Opening of the epoxide (3% perchloric acid in dioxane) then produced the desired 6',7'-dihydroxybergamottin (indicated as compound 2 in FIG. 3) in 70% yield.

SPECIFIC EXAMPLE 3

CYP3A4 Inhibition By 6',7'-dihydroxybergamottin

6',7'-dihydroxybergamottin was evaluated as an inhibitor of CYP3A4 (3A4) in a purified enzyme preparation, as well as against human liver microsomes and human 3A4 expressed in E. coli membrane. In each case, 6',7'-dihydroxybergamottin proved to be a potent NADPH- and time dependent inactivator of 3A4.

Methods

Coexpression of P450 3A4 and reductase in E. coli. The plasmid pB216 containing human P450 3A4 cDNA and human P450 reductase cDNA was transformed into JM 109 cells. Ducharme, M. P. et al., Br. J. Clin. Pharmac. 36:457–459 (1993). The growth of the transformed E. coli was carried out in the modified Terrific Broth and the expression of P450 3A4 and reductase was induced by addition of 1 mM IPTG. δ-Aminolevulinic acid (0.5 mM) was added for heme synthesis. The membrane fraction was prepared from the bacterial cells by sonication after treatment with lysozyme. It was subsequently isolated by differential centrifugation from the bacterial cell homogenate. Ducharme, M. P. et al., Br. J. Clin. Pharmac. 36:457–459 (1993).

Inactivation of P450 3A4 in human liver microsomes and E. coli membranes. The human liver microsomes or the E. coli membrane fractions containing 1 nmol of P450 3A4 were incubated with various concentrations of 6',7'-dihydroxybergamottin in 1 ml of 50 mM Hepes buffer (pH 7.5) containing 2 mM GSH, 1000 U catalase, 0.5 mM EDTA, 30 mM $MgCl_2$ and 20% glycerol at 37° C. for various time periods. At end of the incubation, 100 μl of the incubation mixture was taken for determination of testosterone 6β-hydroxylation activity. The other aliquot was used for P450 determination by the method of Omura and Sato. Ducharme, M. P. et al., Clin. Pharmacol. Ther. 57:485–491 (1995). The human liver microsomes was prepared by differential centrifugation.

Determination of testosterone 6β-hydroxylation. The human liver microsomes or the P450 3A4 and reductase containing E. coli membrane fractions (100 μmol of P450) were incubated with 200 μM testosterone in 1 ml of 50 mM Hepes buffer (pH 7.5). The reactions were initiated by the addition of 1 mM NADPH and terminated by 1 ml of ethyl acetate in ice. The 6β-hydoxytestosterone product was determined by HPLC on a C18 column (Microsorb-MV, 5 μm, 4.6×15 cm) eluted with a mobile phase of 65% of methanol at flow rate of 1 ml/min and the eluate was monitored by UV detection at 254 nm.

Results

Figure 4:
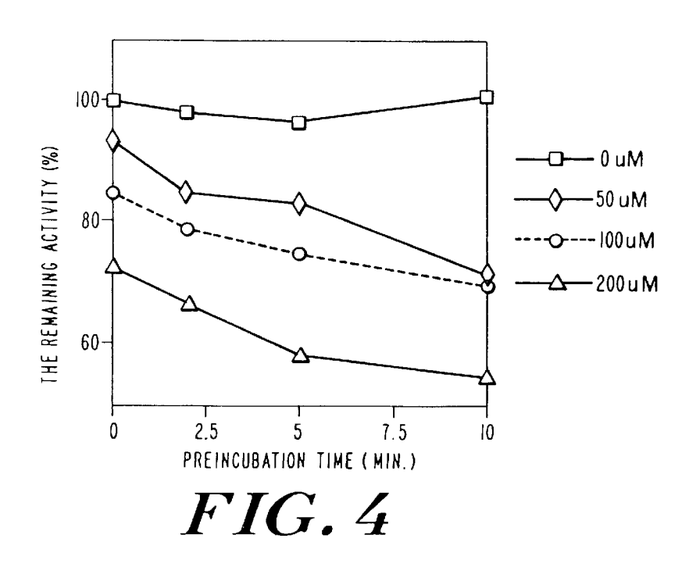
FIG. 4 is a graph showing time and concentration dependent inhibition of testosterone 6β-hydroxylase activity in human liver microsomes by 6',7'-dihydroxybergamottin.

P450 3A4 activity was significantly inhibited by 6',7'-dihydroxybergamottin when either human liver microsomes or E. coli membranes containing the expressed human P450 3A4 and reductase were used. As shown in FIG. 4, the inhibition of 6β-hydroxytestosterone formation activity in human liver microsomes was time and concentration dependent as well as requiring catalytic turnover of 6',7'-dihydroxybergamottin, which suggested that the inhibition resulted from the mechanism based-inactivation of P450 3A4. Guengerich, P. et al., Carcinogenesis 11:2276–2279 (1990). The inactivation appeared to be due to a reaction at the active site because it was not inhibited by the presence of 2 mM GSH in the incubation system. Competitive inhibition of the catalytic activity was also observed for the samples without preincubation where approximately 30% of testosterone 6β-hydroxylase activity was inhibited when 6',7'-dihydroxybergamottin was incubated with human liver microsomes at a final concentration of 20 μM, and about 45% of the activity of the expressed P450 3A4 was inhibited when it was incubated with 6',7'-dihydroxybergamottin in the absence of NADPH (see Table 2). Despite the loss of 70% of the P450 3A4 catalytic activity by preincubation with 6',7'-dihydroxybergamottin and NADPH, human liver microsomes still retained about 90% of the P450 as measured by the reduced-CO spectrum (see Table 2). Similar results were obtained with the E coli. expressed P450 3A4 where 90% of catalytic activity was lost by 90% after preincubation with 6',7'-dihydroxybergamottin and NADPH for 15 min, but there was not any loss of spectrally detectable P450 (see Table 2). Studies on inactivation by another furanocumarin, 8-methoxyporalen, have also shown that there was no heme fragment, MI complex and heme adduct formation in in vivo studies of 8-methoxyporalen treated rats or in in vitro studies of 8-methoxyporalen incubated with rat liver microsomes. (Kronbach, T. et al., *Clin. Pharmac. Ther.* 43:630–635 (1988); Edwards, D. J. et al., *Drug Metab. Dispos.* 24:1287–1290 (1996). But, 8-methoxyporalen was extensively bound to microsomal apoP450, and the binding was only partially diminished by cysteine. Another example involved inactivation of P450 1A1 and 1A2 by coriandrin, a linear furoisocoumarin. In this case, covalent binding of the coriandrin to apoP450 was demonstrated without significant heme. Tatum, J. H. et al., *Phytochemistry* 18:500–502 (1979). Therefore, 6',7'-dihydroxybergamottin-mediated inactivation of P450 3A4 appears to be primarily a result of modification of the apoprotein, as has been observed with 2-or 9-ethynylphenanthrene for the mechanism based inactivation of P450 2B1 and 2B4. Chatterjee, A. et al., *J. Chem. Soc.* 2245–2247 (1961); Schonberg, A. et al., *J. Am. Chem. Soc.* 77:2563–2564 (1955).

TABLE 2

6',7'-dihydroxybergamottin (DHB)-Mediated Inactivation Of P450 3A4*

|  | Testosterone 6-β hydroxylation (nmol/nmol P450/min) | P450 Content (nmol/ml) |
|---|---|---|
| Human liver microsomes |  |  |
| +NADPH/−DHB | 0.54 | 0.94 |
| −NADPH/+DHB | 0.37 | 0.93 |
| +NAHPH/+DHB | 0.18 | 0.87 |
| Coexpressed P450 3A4 with reductase in *E. coli* membrane |  |  |
| +NADPH/−DHB | 8.13 | 1.20 |
| −NADPH/+DHB | 4.45 | 1.16 |
| +NADPH/+DHB | 0.45 | 1.20 |

*Human liver microsomes or the *E. coli.* membrane containing P450 3A4 coexpressed with reductase (1 nmol/ml) were incubated with 400 μM DHB for 15 min at 37° C. in 50 mM Hepes buffer (pH 7.5) containing 30 mM MgCl$_2$, 2 mM GSH, 0.5 mM EDTA, 1000 u/ml of catalase and 20% glycerol.

SPECIFIC EXAMPLE 4

I. Quantification of 6',7'-dihydroxybergamottin in grapefruit and other fruits

Using the high performance liquid chromatographic assay set forth in Specific Example 1, the concentration of 6',7'-dihydroxybergamottin is measured in grapefruit juice (and juice from a number of sources (fresh squeezed from different varieties of grapefruit, commercially prepared juice, juice from frozen concentrate)) and at various times of the year. Other citrus fruits (e.g. sweet oranges, sour oranges (Seville), lemon, pummelo), non-citrus fruits and beverages derived from natural products, such as tea, are screened for the presence of this compound.

II. Absorption and disposition of 6',7'-dihydroxybergamottin

In human subjects, oral administration of grapefruit juice (containing a known amount of 6',7'-dihydroxybergamottin) allows for an estimation of bioavailability from urinary recovery studies. Oral clearance, absorption rate, and elimination half-life are calculated from plasma concentrations. A chronically catherized rat model is used to compare the disposition of 6',7'-dihydroxybergamottin following oral, intraportal and IV administration. Raftogianis, R. B. et al., *J. Pharmacol. Exp. Ther.* 276:602–608 (1996) and Kimura, R. E. et al., *Pediatr.Res.* 23:235–240 (1988). 6',7'-dihydroxybergamottin is incubated with human liver microsomes and metabolic products identified using NMR, mass spectroscopy and other standard techniques.

A. Disposition of 6',7'-dihydroxybergamottin in the rat. The absorption process is relatively consistent between species (Lin, J. H., *Drug Metab. Dispos.* 23:1008 (1995)) and the pharmacokinetic profile in the rat provides valuable information in designing human studies with this compound. Drug is administered intravenously, intraportally or into the duodenum with sampling from the aorta or portal vein for up to 21 days. Raftogianis, R. B. et al., *J. Pharmacol. Exp. Ther.* 276:602–608 (1996) and Kimura, R. E. et al., *Pediatr.Res.* 23:235–240 (1988). Pharmacokinetic parameters such as clearance, volume of distribution and absolute bioavailability require IV administration for precise calculation. In addition, oral and intraportal dosing can distinguish between the gut and liver first-pass metabolism of compounds. This data is particularly relevant for 6',7'-dihydroxybergamottin since it inhibits cytochrome P450 in the intestinal wall.

Male Sprague Dawley rats (175–200 gm) are studied. This strain is widely used to study xenobiotic disposition in rodents. Animals are allowed to acclimatize for 2 weeks before surgery is performed. Animals are anesthetized with 20 mg/ml ketamine intramuscularly followed by 10 mg/kg pentobarbital intraperitoneally. The abdomen and back of the neck are shaved, washed with ethanol and painted with 1% Betadine. Using aseptic technique, a 5 cm vertical midline incision is made from the subxiphoid process to the suprapubic region. Cannulae (hand prepared from silastic tubing, JELCO intravenous catheter placement unit and PE 60 tubing) are placed into the aorta, inferior vena cavae, portal vein and duodenum. Infusion sets are sutured securely to the back of the rat following closing of the abdominal cavity. Catheters are flushed twice daily with 500 u/mL heparin and 4 mg/ml ampicillin. The entire surgical procedure takes approximately 20 minutes. Rats are weighed and monitored daily for signs of distress and infection.

6',7'-dihydroxybergamottin is administered into the duodenum, intravenously and directly into the portal vein. Since the surgical model remains intact for up to 21 days, each animal receives compound by all three routes with a 3 day washout period between treatments. Since preliminary studies indicate that the typical dose of 6',7'-dihydroxybergamottin in a glass of grapefruit juice is roughly 10–15 mg (0.15–0.2 mg/kg), initial experiments use a similar dose (0.2 mg/kg) for all routes of administration. The compound is much more soluble in ethanol than water. In order to minimize the volume to be administered, 6',7'-dihydroxybergamottin is initially dissolved in a small volume of ethanol and diluted to the required concentration with water (final ethanol content is expected to be less than 5%). Animals are free moving but maintained in metabolism cages throughout the experiments. Urine is collected after administration of 6',7'-dihydroxybergamottin to assess urinary recovery of parent compound and metabolites. Blood samples for estimation of standard pharmacokinetic parameters are collected (0.25 ml) at various times for several hours after administration. Finally, samples are obtained from the portal vein following duodenal administration of compound.

Plasma concentrations of 6',7'-dihydroxybergamottin are determined using the HPLC assay described herein. Pharmacokinetic parameters such as clearance, volume of distribution, and elimination half-life are calculated following IV administration using standard non-compartmental techniques (area estimation using the computer program LAGRAN). Bioavailability is calculated for oral and intraportal administration of the drug by comparing the area under the plasma concentration-time curve to that observed with IV administration. Intraportal administration allows for an assessment of the intrinsic clearance of the compound by the liver. A significant difference between oral and intraportal availability suggests poor absorption or gut wall metabolism of 6',7'-dihydroxybergamottin. Samples obtained from the portal vein following duodenal administration determine whether drug is reaching the portal circulation intact. A comparison is also made of the plasma concentration-time profile of 6',7'-dihydroxybergamottin when administered orally as grapefruit juice or purified compound in order to determine whether bioavailability is dependent upon oral formulation. Studies with 8-methoxypsoralen have suggested that formulation is an important determinant of oral bioavailability. Hertog, M. G. L. et al., *Lancet* 342:1007–1011 (1993). Statistical comparisons are made using analysis of variance (when the same parameter is being compared between more than two groups of animals) or the t-test for comparisons between 2 groups. A value of $p<0.05$ is considered to be statistically significant.

B. Disposition of 6',7'-dihydroxybergamottin in humans. Since 6',7'-dihydroxybergamottin is consumed by a significant proportion of the population as part of their usual diet, the oral administration of this compound to humans in the form of grapefruit juice poses no significant ethical or toxicologic risk.

Grapefruit juice is administered initially to twenty healthy non-obese (within 20% of ideal body weight) subjects (male or female) between the ages of 18 and 70 years of age. Subjects are asked to refrain from grapefruit and any other food identified as having a high content of 6',7'dihydroxybergamottin for 1 week prior to study in order to ensure that baseline concentrations of 6',7'-dihydroxybergamottin are not significant. Following an overnight fast, subjects ingest 300 ml of juice prepared from frozen concentrate at approximately 8 am. The concentration of 6',7'-dihydroxybergamottin is determined prior to administration in order to calculate the administered dose. Based on preliminary data, it is expected that 300 ml of juice contains between 10 and 15 mg of 6',7'-dihydroxybergamottin. No food is allowed until 4 hours after administration of grapefruit juice at which time a standard meal (containing foods previously screened and found to be free of 6',7'-dihydroxybergamottin) is given. Initial studies focus on the urinary recovery of 6',7'-dihydroxybergamottin and major metabolites identified by preliminary studies in order to assess the oral bioavailability of the compound. Urine is collected prior to and at timed intervals from 0–2, 2–4, 4–8 and 8–12 hours after juice administration. Concentrations in urine are typical severalfold higher than plasma concentrations for most xenobiotics allowing for a more sensitive assessment of bioavailability. For example, even if only 1% of the administered dose of 6',7'-dihydroxybergamottin is found in the urine, concentrations with typical urine volumes should be in the range of 0.1 mg/L and detectable by the HPLC assay method.

Further studies are conducted with collection of blood after administration of grapefruit juice. Blood samples (5 ml) are collected from an antecubital vein immediately prior to administration of juice and at 0.5, 1.0, 2.0, 3.0, 4.0, 6.0, 8.0 and 12.0 hours after ingestion of juice. Samples at later times may be obtained if preliminary data suggests that the compound has a long half-life. Blood is collected into red top blood collection tubes, allowed to clot and the serum harvested and stored pending analysis. Subjects are allowed water ad libitum throughout the study and standard meals are given at 4 and 10 hours into the study. Plasma and urine are assayed for 6',7'-dihydroxybergamottin concentration using the HPLC assay described herein. Pharmacokinetic parameters are calculated using standard non-compartmental methods. Area under the plasma concentration-time curve is estimated using Lagrange polynomial interpolation. Oral clearance (Cl/F), apparent volume of distribution (Vss/F), elimination half-life, time to reach maximum plasma concentration (tmax) and maximum plasma concentration (Cmax) is calculated from the plasma data.

III. Effect of 6',7'-dihydroxybergamottin on enzymes involved in the oxidation and conjugation of foreign compounds Using isolated pure compound, in vitro studies are conducted with human liver microsomes to determine the specificity, potency and mechanism of inhibitory effects on substrates for the primary cytochrome P450 enzymes involved in pro-carcinogen activation (including, but not limited to, CYP1A1, CYP1A2, CYP2A6, CYP2D6, CYP2E1 and CYP3A4). Since conjugation may also result in bioreactive metabolites, phenol sulfotransferase, UDP-glucuronosyltransferase and glutathione S-transferase activity is measured under control conditions and following incubation with 6',7'-dihydroxybergamottin.

A. Inhibition of cytochrome P450 enzymes by 6',7'-dihydroxybergamottin. Studies are conducted using a similar model as described herein, which have been useful in evaluating the inhibitory effects of grapefruit juice. It has been established that inhibition is concentration-dependent and requires no pre-incubation with microsomes suggesting that 6',7'-dihydroxybergamottin does not have to be converted to a more active form in order to inhibit enzyme activity. However, it is possible that pre-incubation could enhance the inhibitory effects of the compound. Initial mechanistic studies examine the effect of 6',7'-dihydroxybergamottin in the formation of 6β-hydroxytestosterone as a marker of CYP3A activity. Product formation is be compared in the presence of the inhibitor over a wide range of concentrations and the data plotted according the methods of Dixon and Comish-Bowden. Dixon, M., *Biochem. J.* 55:470–471 (1953) and Cornish-Bowden, A., *Biochem. J.* 137:143–144 (1974). Both methods are employed since the Dixon plot allows for discrimination between competitive and uncompetitive inhibition while the Cornish-Bowden plot is superior in distinguishing between competitive and non-competitive inhibition. Comparisons are made between inhibition produced with and without pre-incubation of the inhibitor. In addition, P450 concentration is determined during incubation of 6',7'-dihydroxybergamottin with microsomes in order to examine the hypothesis that the compound may exhibit mechanism-based inhibition.

The specificity and potency of 6',7'-dihydroxybergamottin inhibition of individual P450 enzymes is studied by measuring the rates of metabolism of known substrates for specific enzymes. These include ethoxyresorufin deethylase (CYP1A1 and CYP1A2), (Burke, M. D. et al., *Biochem. Pharmacol.* 34:3337–3345 (1985)) coumarin 7-hydroxylation (CYP2A6), (Greenlee, W. F. et al., *J. Pharmacol. Exp. Ther.* 205:596–605 (1978)) bufuralol 1-hydroxylation (CYP2D6), (Brian, W. R. et al., *Biochemistry* 29:11280–11292 (1990)) chlorzoxazone 6-hydroxylation (CYP2E1) (Peter, R. et al., *Chem. Res. Toxicol.* 3:566–573 (1990)) and testosterone 6β-hydroxylation (CYP3A4). Sonderfan, A. J. et al., *Arch. Biochem. Biophys.* 255:27–41 (1987). Individual cDNA-expressed human cytochrome P450 enzymes are obtained from Gentest Corporation (Woburn, Mass.) and incubated with substrate and NADPH-regenerating system. 6',7'-dihydroxybergamottin is added to the incubation mixture over a wide range of concentrations in order to determine the concentration required to reduce the rate of the reaction by 50% ($IC_{50}$) for each of the common cytochrome P450 enzymes. For comparison, $IC_{50}$ values are determined for known specific inhibitors of each of these enzymes (e.g. furafylline (CYP1A2), quinidine (CYP2D6), ketoconazole (CYP3A4)).

B. Effect of 6',7'-dihydroxybergamottin on substrate conjugation. Galinsky and co-workers Raftogianis, R. B. et al., *J. Pharmacol. Exp. Ther.* 276:602–608 (1996) have examined the effect of total parenteral nutrition on hepatic drug conjugation in vitro and in vivo. Since the effect of grapefruit juice or 6',7'-dihydroxybergamottin on drug conjugation has not been previously studied, experiments are conducted in vitro in order to assess the need for follow-up studies in humans or animals.

Microsomal or cytosolic fractions are prepared from male Sprague-Dawley rats according to established procedures. Raftogianis, R. B. et al., *J. Pharmacol. Exp. Ther.* 276:602–608 (1996). Cytosolic glutathione S-transferase activity is assessed under control conditions and with varying concentrations of 6',7'-dihydroxybergamottin using 1-chloro-2,4-dinitrobenzene as substrate. Acetaminophen and p-nitrophenol are used as substrates for phenol sulfotransferase in cytosol and for assessment of glucuronosyltransferase activity in microsomes. Raftogianis, R. B. et al., *J. Pharmacol. Exp. Ther.* 276:602–608 (1996); Habig, W. H. et al., *J. Biol. Chem.* 249:7130–7139 (1974) and Ritter, J. K. et al., *Drug Metab. Dispos.* 15:335–343 (1987). Sulfotransferase activity towards acetaminophen is determined in 0.1M citric acid-0.2M sodium phosphate buffer (pH 5.7) containing 5–10 mg/ml cytosolic protein, 500 $\mu$M PAPS, and 600 $\mu$M acetaminophen. The reaction is terminated by addition of perchloric acid after a 10 minute incubation at 25 C. Acetaminophen sulfate is measured by HPLC. Corcoran, G. B. et al., *J. Pharmcol. Exp. Ther.* 232:857–863 (1985). For determination of the glucuronidation of acetaminophen, the incubation mixture consists of 50 mM tris buffer (pH 7.85) containing 150 mM KCl, 10 mM $MgCl_2$, 2 mg/mL microsomal protein, 60 mM acetaminophen and 0.05% Triton X-100. The reaction is initiated through addition of 5 mM UDPGA and terminated after 15 minutes at 37 C. by addition of perchloric acid.

SPECIFIC EXAMPLE 5

Cyclosporine is widely used as an immunosuppressant drug in order to prevent rejection following transplantation. Although highly effective, there are significant problems with the use of cyclosporine. It is an extremely expensive drug with annual treatment costs which can be in the range of several thousand dollars per patient. In addition, it is difficult to titrate the dosage to provide adequate immunosuppression with minimal toxicity in part due to the poor and highly variable bioavailability as a result of CYP3A-mediated gut wall metabolism of the drug. Grapefruit juice containing 6',7'-dihydroxybergamottin has been demonstrated to increase the bioavailability of cyclosporine by about 50%. Larger increases would be anticipated with doses of 6',7'-dihydroxybergamottin larger than can be ingested conveniently in the form of grapefruit juice (approximately 10–20 mg). Increased bioavailability reduces the dosage requirement of cyclosporine (a dosage reduction of at least one-third would be expected with the administration of approximately 5–20 mg of 6',7'-dihydroxybergamottin). Moreover, an improvement in the extent of drug availability is typically accompanied by more consistent, less variable bioavailability. This results in more consistency in blood concentrations and makes it easier for the clinician to achieve an optimal dosage.

Typically, cyclosporine is administered chronically at a dosage of 3–10 mg/kg/day with the dosage declining over time as the risk of transplantation rejection decreases. The daily dose is generally divided for administration twice daily. Dosage is adjusted based on measured blood concentrations for cyclosporine designed to produce concentrations of 100 to 400 ng/mL (using assays specific for cyclosporine). Patients receiving cyclosporine in combination with 6',7'-dihydroxybergamottin would initially be started on a regimen of 6',7'-dihydroxybergamottin 10 mg in the morning and 10 mg in the evening with each dose of 6',7'-dihydroxybergamottin to be given concomitantly with a dose of cyclosporine. The starting dose of cyclosporine would be two-thirds of the usual starting dose in anticipation of a 50% improvement in bioavailability. The dosage of 6',7'-dihydroxybergamottin as well as cyclosporine would be adjusted based on measured blood concentrations. For example, if blood concentrations of cyclosporine are low, the dosage of 6',7'-dihydroxybergamottin would be increased in order to increase the degree of inhibition, bioavailability and blood concentrations. If blood concentrations are too high, the dosage of cyclosporine would be further lowered.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, specification and claims.

All publications cited herein are expressly incorporated by reference.

We claim:

1. A pharmaceutical preparation in unit dosage form adapted for administration to decrease cytochrome P450 activity comprising from about 5 to about 20 mg 6',7'-dihydroxybergamottin, substantially free of other grapefruit juice constituents.

2. The pharmaceutical preparation of claim 1, wherein the unit form is adapted for oral administration.

3. The pharmaceutical preparation of claim 2, wherein the form adapted for oral administration is a tablet.

4. A composition comprising a therapeutically-effective amount of 6',7'-dihydroxybergamottin substantially free of other grapefruit juice constituents, in a pharmaceutically-acceptable carrier.

5. The composition of claim 4, wherein the therapeutically-effective amount of 6',7'-dihydroxybergamottin is from about 5 to about 20 mg.

6. A composition comprising a therapeutically-effective amount of 6',7'-dihydroxybergamottin substantially free of other grapefruit juice constituents, in a pharmaceutically-acceptable delivery system for in vivo delivery.

7. The composition of claim 6, wherein the therapeutically-effective amount of 6',7'-dihydroxybergamottin is from about 5 to about 20 mg.

8. A method of decreasing cytochrome P450 enzyme activity in a human or other mammal comprising the step of administering to the human or mammal, a therapeutically-effective amount of at least one agent selected from the group consisting of 6',7'-dihydroxybergamottin substantially free of other grapefruit juice constituents, pharmaceutically-acceptable salts of 6',7'-dihydroxybergamottin and combinations thereof.

9. The method of claim 8, wherein the step of administration comprises oral administration.

10. The method of claim 8, wherein the agent is 6',7'-dihydroxybergamottin.

11. The method of claim 8, wherein the agent is 6',7'-dihydroxybergamottin and the therapeutically-effective amount is from about 5 to about 20 mg.

12. The method of claim 8, wherein the cytochrome P450 enzyme is a CYP3A enzyme.

13. A method for increasing the bioavailability of a drug administered to a human or mammal, wherein the drug is metabolized by cytochrome P450 enzyme, comprising the step of administering to the human or mammal a therapeutically-effective amount of an agent selected from the group consisting of 6',7'-dihydroxybergamottin substantially free of other grapefruit juice constituents, pharmaceutically-acceptable salts of 6',7'-dihydroxybergamottin, and combinations thereof.

14. The method of claim 13, wherein the step of administering comprises oral administration.

15. The method of claim 13, wherein the agent is 6',7'-dihydroxybergamottin.

16. The method of claim 13, wherein the agent is 6',7'-dihydroxybergamottin and the therapeutically-effective amount is from about 5 to about 20 mg.

17. The method of claim 13, wherein the cytochrome P450 enzyme is a CYP3A enzyme.

18. The method of claim 13, wherein the drug is cyclosporine.

19. A method for increasing the bioavailability of a drug in a human or mammal, wherein the drug is metabolized by cytochrome P450 enzyme, comprising the steps of:

a) administering to the human or mammal the drug; and b) administering to the human or mammal a therapeutically-effective amount of an agent selected from the group consisting of 6',7'-dihydroxybergamottin substantially free of other grapefruit juice constituents, pharmaceutically-acceptable salts of 6',7'-dihydroxybergamottin, and combinations thereof.

20. The method of claim 19, wherein steps a) and b) are performed simultaneously.

21. The method of claim 19, wherein the agent is 6',7'-dihydroxybergamottin.

22. The method of claim 19, wherein the agent is 6',7'-dihydroxybergamottin and the therapeutically-effective amount is from about 5 to about 20 mg.

23. The method of claim 19, wherein steps a) and b) comprise oral administration.

24. The method of claim 19, wherein the cytochrome P450 enzyme is a CYP3A enzyme.

25. The method of claim 19, wherein the drug is cyclosporine.

* * * * *

UNITED STATES PATENT AND TRADEMARK OFFICE
CERTIFICATE OF CORRECTION

PATENT NO. : 6,160,006
DATED : December 12, 2000
INVENTOR(S) : David J. Edwards and Patrick M. Woster It is certified that error appears in the above-identified patent and that said Letters Patent is hereby corrected as shown below:

ON THE TITLE PAGE
Item [54] Title should read --

6'7'-DIHYDROXYBERGAMOTTIN, A
    CYTOCHROME P450 INHIBITOR IN
    GRAPEFRUIT JUICE --.

Signed and Sealed this

Twenty-ninth Day of May, 2001

Attest:

NICHOLAS P. GODICI

Attesting Officer    Acting Director of the United States Patent and Trademark Office